United States Patent
Tabe et al.

(10) Patent No.: US 6,949,668 B2
(45) Date of Patent: Sep. 27, 2005

(54) PROCESS FOR PRODUCING 5-(3-CYANOPHENYL)-3-FORMYLBENZOIC ACID COMPOUND

(75) Inventors: Masayasu Tabe, Tokyo (JP); Toru Minoshima, Iwakuni (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/497,105

(22) PCT Filed: Nov. 30, 2001

(86) PCT No.: PCT/JP01/10521
§ 371 (c)(1),
(2), (4) Date: May 28, 2004

(87) PCT Pub. No.: WO03/048111
PCT Pub. Date: Jun. 12, 2003

(65) Prior Publication Data
US 2005/0014966 A1 Jan. 20, 2005

(51) Int. Cl.$^7$ ............................ C07C 253/30
(52) U.S. Cl. ................................ 558/359
(58) Field of Search ......................... 558/359

(56) References Cited

FOREIGN PATENT DOCUMENTS

| EP | 1 046 640 A2 | 10/2000 |
|---|---|---|
| EP | 1 179 527 A1 | 2/2002 |
| JP | 7-17937 A | 1/1995 |
| JP | 2000-336090 A | 12/2000 |
| JP | 2001-335555 A | 12/2001 |
| WO | WO 99/269818 A1 | 6/1999 |
| WO | WO 00/69811 A | 11/2000 |
| WO | WO 00/69811 A1 | 11/2000 |

OTHER PUBLICATIONS

A.J. Hoefnagel, et al. "Substituent Effect, Part II, Anomalous Dissociation Constants of Benzoic Acids in Water–Organic Solvent Mixtures, An Extended Hammett Equation Comprising the Hydrophobic Constant as an Additional Parameter", *J. Chem. Soc. Perkin Trans. II*, No. 2, 1989, pp. 977–986, XP002303391.
H. Feulner, et al. Chem Ber., vol. 123, 1989, pp. 1841–1843, XP002199198.
K. Netzke, et al. Chem Ber., vol. 122, 1989, pp. 1365–1371, XP002303422.
Database Caplus Chemical Abstracts Service, Columbus Ohio, XP002303392, Database accession No. 2001:874392.
Andrzej Prewysz–Kwinto, Syntheses of 2,3–Diformylbenzofuran, Part I. Synthesis of 2,3–Diformyl–5–methylbenzofuran and Its Derivative, Polish Journal of Chemistry, 53, pp. 1889–1893 (1979).
The Attachment of One Hydrocarbon Group to Boron, The Organic Chemistry of Boron, Chapater V, pp. 58–64 (1961).
Jacqueline C. Bussolari and Diana C. Rehborn, Preparation of 5–Aryl Furfurals and Aryl Thiophene–2–carboxaldehydes via Palladium–Catalyzed C–C Bond Formation in Aqueous Media, Organic Letters, 1999, vol. 1, No. 7, pp. 965–967 (1999).

*Primary Examiner*—Kamal A. Saeed
(74) *Attorney, Agent, or Firm*—Sughrue Mion, PLLC

(57) ABSTRACT

A 5-(3-cyanophenyl)-3-formylbenzoic acid compound of the formula (IV) is prepared by reacting a 5-bromo-3-(hydroxymethyl)benzoic acid compound of the formula (I) with manganese dioxide to provide a 5-bromo-3-formylbenzoic acid compound of the formula (II), and then reacting the resultant compound of the formula (II) with 3-cyanophenylboronic acid of the formula (III) in the presence of a palladium complex.

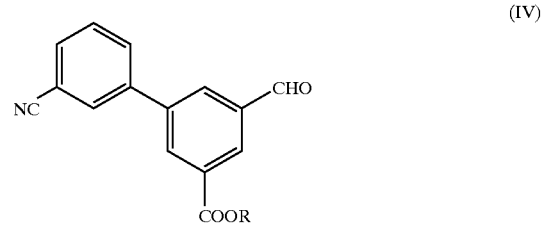

(IV)

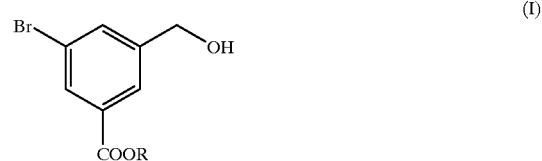

(I)

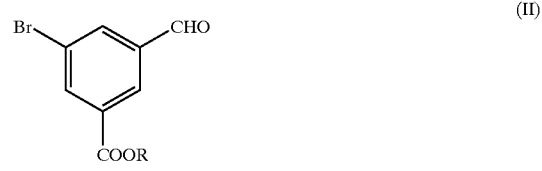

(II)

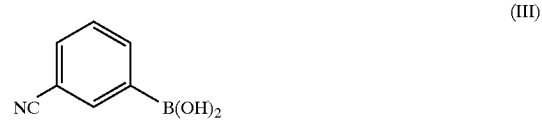

(III)

R is a H atom or a $C_1$–$C_{10}$ alkyl group.

5 Claims, No Drawings

US 6,949,668 B2

PROCESS FOR PRODUCING 5-(3-CYANOPHENYL)-3-FORMYLBENZOIC ACID COMPOUND

TECHNICAL FIELD OF THE INVENTION

The present invention relates to a process for producing a 5-(3-cyanophenyl)-3-formylbenzoic acid compound. More particularly, the present invention relates to a process for producing a 5-(3-cyanophenyl)-3-formylbenzoic acid compound by procedures, which can be easily carried out in industrial practice, with high yields and with low costs.

A 5-(3-cyanophenyl)-3-formylbenzoic acid compound is useful as an intermediate of a clinically applicable inhibitor against selective, activated blood coagulation factor X (which will be referred to as $FX_a$ hereinafter).

BACKGROUND ART

Currently, as thrombosis inhibitors, antithrombin agents are employed. The antithrombin agents exhibit, together with the anticoagulation activity for blood, an inhibiting activity against the platelet-coagulation effect of thrombin. Therefore, it is known that the antithrombin agents may exhibit a tendency to promote bleeding, and thus the control of the inhibiting effect the conventional thrombin agents against the blood coagulation is not easy.

In view of the above-mentioned prior art, it is now attempted to develop a new blood coagulation-inhibiting agent on a basis of an activation mechanism different from that of the blood coagulation-inhibiting activity of the conventional thrombin agents. For example, WO 99/26918 discloses biphenylamidine derivatives having an anti blood-coagulation activity.

As a method of synthesizing a compound having a biphenyl skeleton and useful as an intermediate of the biphenylamidine derivative useful as an $FX_a$ inhibitor, WO 99/26918 discloses a method comprising preparing 3-cyanophenylboronic acid from 3-bromobenzonitrile and subjecting the 3-cyanophenylboronic acid to a coupling reaction with 3-iodo-3-(hydroxymethyl)benzoic acid compound, to provide a 5-(3-cyanophenyl)-3-hydroxymethylbenzoic acid compound. This method, however is industrially disadvantageous in that the synthesis of 3-cyanophenylboronic acid needs a reaction at an extremely low temperature of −78° C., and this extremely low temperature reaction is difficult to effect in industrial practice, that the coupling reaction needs to employ an iodine compound which is expensive, and that the resultant target compound must be purified by using a column chromatography which is difficult to use in industrial practice. Further, each reaction step of the above-mentioned method has problems which are difficult to solve.

As a synthesis method of a phenylboronic acid compound, a method in which a halogenated benzene derivative is converted to an organic metal compound of the derivative and then the organic metal compound reacts with a trialkyl borate, is known from, for example, "The Chemistry of Boron", Academic, New York, 1961; "Methods of Elemento-Organic Chemistry, North-Holland, Amsterdam, 1976, Vol. 1; "Organoborane Chemistry", Academic, New York, 1975, etc.

In the above-mentioned method using the organic metal compound in the case where the organic metal compound is a lithium compound, the reaction of the lithium compound with the trialkyl borate must be conducted at an extremely low temperature of −78° C. Also, in the case where the organic metal compound is a Grignard reagent and in the case where the halogenated benzene derivative has, as a substituent group, a cyano group, it is difficult to prepare a boronic acid compound from the Grignard reagent.

Also, Japanese Unexamined Patent Publication No. 7-17937 discloses a method of selectively reducing only one of two ester groups in an aromatic diester compound. However, this method is disadvantageous in that when this method is utilized to synthesize 5-bromo-3-hydroxymethylbenzoric acid derivative from a 5-bromoisophthalic acid derivative, a side reaction by which both the ester groups of the isophthalate diester are reduced to produce, as a by-product, 5-bromo-3-hydroxymethylbenzyl alcohol in a yield of about 10 molar %, occurs. To remove the by-product, a product of any one of the succeeding procedures must be subjected to a column chromatography which is difficult to be conducted in industrial practice.

The coupling reaction of the boronic acid compound with a halogenated aromatic compound is generally known as a SUZUKI coupling reaction. (Referential documents: Acvavces in Metal-Organic Chemistry, JAI Press Inc, Vol. 6, page 187–243, Organic Lettes., Vol. 1, No. 7, page 965–967 (1999), etc.). With respect to this coupling reaction, WO 00/69811 discloses that the employment of tetrabutylammonium bromide causes the reaction to be completed within a short time. However, a new method enabling the efficiency of the coupling reaction to be enhanced without using the tetrabutylammonium bromide, is desired.

Various methods of oxidizing the aromatic compound having a hydroxymethyl group with manganese dioxide, which is cheap, in a reaction medium comprising methylene chloride, to convert the hydroxymethyl group to a formyl group are known. (Referential documents: Polish J. Chem., 53, 1889 (1975) and Lectures of Experimental Chemistry, Vol. 23, page 21.) These conventional methods are disadvantageous in that the employment of methylene chloride having a low boiling temperature causes a recovery of methylene chloride to be difficult and methylene chloride is harmful to the human body. Accordingly, it is desired to develop a new method in which a reaction medium different from methylene chloride and free from the above-mentioned disadvantages is employed in place of methylene chloride.

DISCLOSURE OF THE INVENTION

An object of the present invention is to provide a process for producing a 5-(3-cyanophenyl)-3-formylbenzoic acid compound, by a easy procedure, with a high yield and with a low cost.

The above-mentioned object can be obtained by the process of the present invention for producing a 5-(3-cyanophenyl)-3-formylbenzoic acid compound.

The process of the present invention for producing a 5-(3-cyanophenyl)-3-formylbenzoic acid compound comprises the steps of:

reacting a 5-bromo-(3-hydroxymethyl)benzoic acid compound represented by the formula (I):

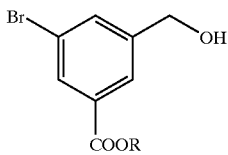
(I)

in which formula (I), R represents a hydrogen atom or a linear or branched chain alkyl group having 1 to 10 carbon atoms, with manganese dioxide, to prepare a 5-bromo-3-formylbenzoic acid compound represented by the formula (II):

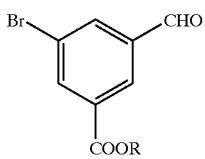
(II)

in which formula (II), R is as defined above; and reacting the resultant 5-bromo-3-formylbenzoic acid compound with 3-cyanophenylboronic acid represented by the formula (III):

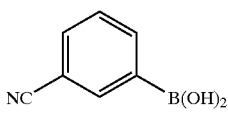
(III)

in the presence of a palladium complex, to prepare a 5-(3-cyanophenyl)-3-formylbenzoic acid compound represented by the formula (IV):

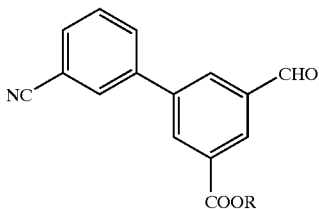
(IV)

in which formula (IV), R is as defined above.

In the process of the present invention for producing a 5-(3-cyanophenyl)-3-formylbenzoic acid compound, the 3-cyanophenylboronic acid represented by the formula (III) is preferably one prepared by reacting 3-formylphenylboronic acid represented by the formula (V):

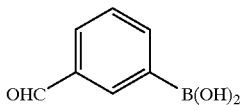
(V)

with hydroxyamine hydrochloride.

In the process of the present invention for producing a 5-(3-cyanophenyl)-3-formylbenzoic acid compound, the 3-formylphenylboronic acid represented by the formula (V) is preferably one prepared by reacting a 3-(dialkoxymethyl)bromobenzene represented by the formula (VI):

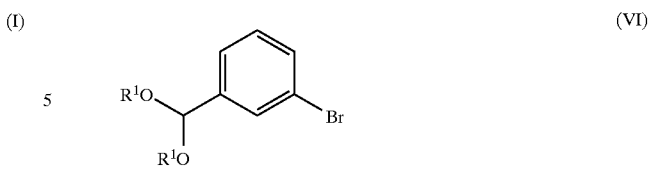
(VI)

in which formula (VI), $R^1$ represents a linear or branched chain alkyl group having 1 to 4 carbon atoms, with magnesium metal to prepare an organic magnesium compound of the 3-(dialkoxymethyl)bromobenzene; and then further reacting the resultant organic magnesium compound with a trialkyl borate.

In the process of the present invention for producing a 5-(3-cyanophenyl)-3-formylbenzoic acid compound, the 5-bromo-3-(hydroxymethyl)benzoic acid compound represented by the formula (I) is preferably one prepared by reacting a 5-bromoisophthalic acid compound represented by the formula (VII):

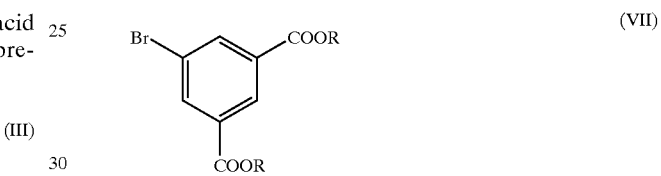
(VII)

in which formula (VII), R is as defined above, with sodium borohydride.

In the process of the present invention for producing a 5-(3-cyanophenyl)-3-formylbenzoic acid compound, the 5-bromo-3-(hydroxymethyl)benzoic acid compound prepared by the reaction of the 5-bromoisophthalic acid compound represented by the formula (VIII) with sodium borohydride, is preferably purified by using a mixed solvent comprising an alcohol and a benzene derivative.

BEST MODE FOR CARRYING OUT THE INVENTION

The process of the present invention for producing a 5-(3-cyanophenyl)-3-formylbenzoic acid compound comprises:

(A) a step of reacting a 5-bromo-3-(hydroxymethyl) benzoic acid compound represented by the formula (I):

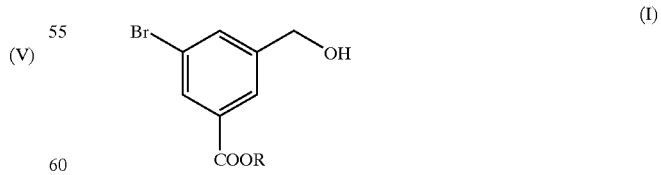
(I)

in which formula (I), R represents a hydrogen atom or a linear or branched chain alkyl group having 1 to 10 carbon atoms, with manganese dioxide, to prepare a 5-bromo-3-formylbenzoic acid compound represented by the formula (II):

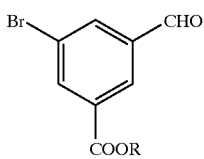

(II)

in which formula (II), R is as defined above; and (B) a step of reacting the resultant 5-bromo-3-formylbenzoic acid compound with 3-cyanophenylboronic acid represented by the formula (III):

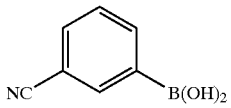

(III)

in the presence of a palladium complex, to prepare a 5-(3-cyanophenyl)-3-formylbenzoic acid compound represented by the formula (IV):

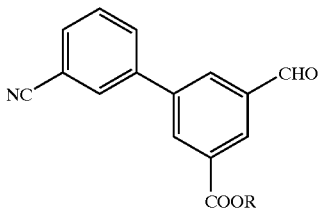

(IV)

in which formula (IV), R is as defined above.

In the above-mentioned step (A), the 5-bromo-3-(hydroxymethyl)benzoic acid compound of the formula (I) includes 5-bromo-3-(hydroxymethyl)benzoic acid and $C_1$–$C_{10}$ linear or branched alkyl esters of the acid. Namely, in the formula (I), R represents a hydrogen atom or a $C_1$–$C_{10}$ linear or branched alkyl group. The reaction of the 5-bromo-3-(hydroxymethyl)benzoic acid compound with manganese dioxide is preferably carried out in an organic solvent comprising at least one member selected from, for example, toluene, xylene, ethyl acetate, acetone, methylethylketone (MEK) and tetrahydrofuran (THF). In this reaction, the reaction temperature is preferably in the range of from 30 to 180° C., more preferably, from 80 to 150° C. This reaction may be carried out under the ambient atmospheric pressure, a reduced pressure or an increased pressure. Usually, the reaction is preferably conducted under the ambient atmospheric pressure. Also, the reaction time can be appropriately established in response to the reaction temperature, usually is preferably in the range of from 0.5 to 10 hours.

In the step (A), manganese dioxide is preferably employed in a molar amount of 2 to 15 times, more preferably 4 to 8 times, that of the 5-bromo-3-(hydroxymethyl)benzoic acid compound. If the manganese dioxide is employed in a molar amount of less than 2 times that of the benzoic acid compound, the reaction may not be completed within a practically applicable reaction time, and thus portions of the starting compounds may remain unreacted. Also, if manganese dioxide is used in a molar amount of more than 15 times the benzoic acid compound, additional by-products may be generated.

In the reaction step (A) of the process of the present invention, the hydroxymethyl group of the 5-bromo-3-(hydroxymethyl)benzoic acid compound of the formula (I) is oxidized with manganese dioxide and converted to a formyl group, to prepare a 5-bromo-3-formylbenzoic acid compound. After the reaction is completed, the reaction mixture liquid is cooled to room temperature and filtered. The resultant filtrate liquid is concentrated to obtain 5-bromo-3-formylbenzoic acid compound.

In the reaction step (B) of the process of the present invention, the 5-bromo-3-formylbenzoic acid compound of the formula (II) prepared in the step (A) is reacted with 3-cyanophenylboronic acid of the formula (III) in the presence of a palladium complex (a catalyst) to prepare the target compound, namely a 5-(3-cyanophenyl)-3-formylbenzoic acid compound of the general formula (IV). The palladium complex is preferably selected from, for example, zerovalence palladium complexes, for example, tetrakistriphenylphosphine palladium and divalence palladium complexes, for example, palladium diacetate, palladium dichloride and bistriphenylphosphine palladium dichloride, and palladium diacetate is more preferably employed for the present invention. The palladium complex is preferably employed in a molar amount of 0.001 to 50 molar %, more preferably 0.1 to 5 molar %, on the basis of the molar amount of the 5-bromo-3-formylbenzoic acid compound used in the reaction step (B). If the amount of the palladium catalyst present in the reaction of the step (B) is less than 0.001 molar % on the basis of the molar amount of the 5-bromo-3-formylbenzoic acid compound, the reaction time necessary to complete the reaction may become too long, and if the amount of the palladium catalyst is more than 50 molar %, the resultant target compound may be difficult to purify. The reaction mixture for the reaction step (B) preferably contain a basic compound as a neutralizing agent. For the basic compound, at least one member selected from sodium hydrogen carbonate, potassium hydrogen carbonate, potassium carbonate and potassium phosphate hydride is preferably employed. Among these compounds, sodium hydrogen carbonate and/or potassium hydrogen carbonate is preferably employed. The basic compound is preferably employed in a molar amount of 2 to 5 times, more preferably 2 to 4 times, the molar amount of the 3-cyanophenylboronic acid. The reaction solvent for the reaction step (B) preferably comprises at least one member selected from water-containing dimethylformamide, water-containing dimethylacetamide, water-containing N-methylpyrrolidone, water-containing N,N-dimethylimidazolidinone and water-containing THF. Particularly, the water-containing dimethylformamide is more preferably employed.

The reaction of the step (B) is preferably conducted in a non-reactive gaseous atmosphere, for example, an atmosphere of an inert gas, for example, an argon gas atmosphere or nitrogen gas atmosphere. The reaction temperature of the step (B) is preferably 30 to 150° C., more preferably 50 to 100° C. Also, the reaction pressure of the step (B) may be any one of the ambient atmospheric pressure, reduced pressures and increased pressures, and usually, the ambient atmospheric pressure is preferably applied to the reaction of the step (B). The reaction time for the step (B) is appropriately established in response to the reaction temperature and usually is preferably in the range of from 0.1 to 24 hours, more preferably from 0.5 to 10 hours.

After the reaction of the step (B) is completed, the resultant reaction mixture liquid is filtered under hot conditions, the resultant filtrate liquid is heated to a temperature of 50 to 100° C., water is added to the heated reaction mixture liquid, the resultant precipitates are collected by, for example, filtration, to obtain the target compound.

Optionally, the collected precipitate is heat-dissolved in a water-containing tetrahydrofuran (THF) at a temperature of 50 to 100° C. and the resultant solution is mixed with an alkyl alcohol having 1 to 3 carbon atoms to recrystallize and purify the target compound.

The water-containing THF preferably has a water content of 0.5 to 10% by mass, more preferably 1 to 5% by mass. The water-containing THF is preferably employed in an amount by mass of 1 to 6 times the mass of the collected precipitate. The alkyl alcohol is preferably selected from methyl alcohol, ethyl alcohol, 2-propyl alcohol and 1-propyl alcohol. Particularly, 2-propyl alcohol is preferably employed to purify the target compound. The alkyl alcohol is preferably employed in an amount by mass of 1 to 10 times the mass of the water-containing THF.

The 5-bromo-3-(hydroxymethyl)benzoic acid compound of the general formula (I) usable for the reaction step (A) of the process of the present invention may be produced by a conventional production process. The compound is preferably one produced by a reaction of a 5-bromoisophthalic acid compound represented by the general formula (VII) with sodium borohydride ($NaBH_4$). Preferably, sodium borohydride for the above-mentioned reaction is employed in a molar amount of 0.5 to 2 times, more preferably 0.8 to 1.4 times, the molar amount of the 5-bromo-isophthalic acid compound of the formula (VII). If the molar amount of sodium borohydride is less than 0.5 time the molar amount of the compound of the formula (VII), the reaction may not completed within a practical reaction time, and if the molar amount of NaBH4 is more than 2 times that of the compound of the formula (VII), the generation of by-products may occur in too large a yield. The reaction pressure may be the ambient atmospheric pressure, a reduced pressure or an increased pressure. Usually, the reaction is preferably carried out under the ambient atmospheric pressure. The reaction procedure is preferably carried out in a reaction solvent comprising at least one member selected from, for example, tetrahydrofuran, diethyl ether and dioxane.

The resultant 5-bromo-3-(hydroxymethyl)benzoic acid compound from the above-mentioned reaction can be isolated from the reaction mixture liquid by, for example, an extraction procedure. The extracting medium may comprise an acetate ester solvents, for example, ethyl acetate, methyl acetate or isopropyl acetate; aromatic solvents, for example, toluene and xylene; ether solvents, for example, THF and diethylether; and ketone solvents, for example, methylethylhetone.

The crude product of 5-bromo-3-(hydroxymethyl)benzoic acid compound isolated from the reaction mixture liquid by the above-mentioned procedure contains, as a reaction by-product, 5-bromo-3-(hydroxymethyl)benzyl alcohol. To purify the 5-bromo-3-(hydroxymethyl)benzoic acid compound by separation removing the by-product, the crude product of the 5-bromo-3-(hydroxymethyl)benzoic acid compound is further purified by using a mixed solvent comprising an alcohol and a benzene derivative. The above-mentioned alcohol include methyl alcohol, ethyl alcohol and/or ethylene glycol. Among then, methyl alcohol, which has a high solubility in water and in benzene derivatives and a high dissolving property to the by-product, is preferably employed. The benzene derivatives for the mixed solvent preferably comprises an alkylated benzene compound, for example, xylene, or toluene. More preferably, xylene having a high dissolving property for alcohols is employed.

In the above-mentioned purifying procedure, the crude product of the 5-bromo-3-(hydroxymethyl)benzoic acid compound is dissolved in an alcohol, for example, methyl alcohol, the solution is mixed with water, the resultant mixture liquid is mixed with a benzene derivative, for example, toluene or xylene, to extract the 5-bromo-3-(hydroxymethyl)benzoic acid compound in an organic phase fraction of the mixture liquid. The resultant extract liquid is washed, dried and concentrated to collect the purified 5-bromo-3-(hydroxymethyl)benzoic acid compound.

3-cyanophenylboronic acid of the formula (III) usable for the step (B) of the process of the present invention may be produced by an appropriate method. Preferably, 3-cyanophenylboronic acid is produced by reacting 3-formylphenylboronic acid of the formula (V) with hydroxylamine hydrochloride. In this production method, the reaction of 3-formylphenylboronic acid with hydroxylamine hydrochloride is preferably conducted in an organic solvent comprising at least one member selected from formic acid, acetic acid and propionic acid, more preferably in formic acid. The organic solvent is preferably used in an amount by mass of 5 to 15 times the amount by mass of the 3-formylphenylboronic acid subjected to the reaction. Also, this reaction is carried out at a reaction temperature of 90° C. to the heat-refluxing temperature of the reaction for a reaction time of 0.5 to 24 hours, more preferably 5 to 8 hours. After the completion of the reaction, the target compound, for example, 3-cyanophenylboronic acid of the formula (III), can be collected from the resultant reaction mixture by recrystallizing the target compound. The above-mentioned production method of 3-cyanophenylboronic acid does not need to be carried out at an extremely low temperature and can be effected by a simple reaction procedure, and thus the resultant 3-cyanophenylboronic acid from this method is advantageous in a high degree of purity thereof.

3-formylphenylboronic acid of the formula (V) usable as a starting material for the production reaction of the above-mentioned 3-cyanophenylboronic acid may be produced by an appropriate method. Particularly, it is preferable that 3-formylphenylboronic acid be one produced by reacting 3-(dialkoxymethyl)bromobenzene, in which the alkyl group in the alkoxyl group in the alkoxymethyl group is preferably selected from $C_1$–$C_4$ linear and branched alkyl groups, more preferably methyl and ethyl groups, with metallic magnesium to prepare an organic magnesium compound thereof, and then reacting the organic magnesium compound with a trialkyl borate compound. The reaction for the preparation of the above-mentioned organic magnesium compound is carried out in an organic solvent which is not limited to a specific type of solvent as long as the solvent can dissolve therein 3-(dialkoxymethyl)bromobenzene, and is inert to the reaction of the 3-(dialkoxymethyl)bromobenzene with the magnesium metal. Usually, the organic solvent preferably comprises an ether selected from, for example, diethylether, tetrahydrofuran, tert-butylmethylether, and diisopropylether or a mixture of the above-mentioned ether compounds, more preferably diethylether, tetrahydrofuran, tert-butylmethylether or a mixture thereof. The metallic magnesium is preferably used, for the reaction, in a molar amount of 0.6 to 3 times the molar amount of the 3-(dialkoxymethyl)bromobenzene.

If the metallic magnesium is used in a molar amount of less than 0.6 times, the target compound may be obtained in an unsatisfactory yield, and if the magnesium metal is used in a molar amount of more than 3 times, undesired by-products may be produced and the resultant reaction mixture may be difficult to after-treato. The reaction with the magnesium metal in preferably carried out at a temperature of 0 to 100° C. for a time of 0.5 to 24 hours, more preferably at 10 to 80° C. for 0.5 to 10 hours. This reaction may be carried out under any pressure condition, for example, the ambient atmospheric pressure, a reduced pressure or an increased pressure. Usually, the reaction is preferably carried out under the ambient atmospheric pressure.

The resultant organic magnesium compound from the above-mentioned reaction is subjected to a reaction with a trialkyl borate. The trialkyl borate usable for the reaction is preferably selected from, for example, trimethyl borate, triethyl borate, triisopropyl borate and tri-n-butyl borate, more preferably trimethyl borate.

The reaction of the organic magnesium compound with a trialkyl borate compound is preferably carried out at a reaction temperature of −70° C. to +20° C. for a reaction time of 0.5 to 24 hours, more preferably at −10 to +20° C. for 0.5 to 12 hours.

The above-mentioned process for producing 3-formylphenylboronic acid compound is advantageous in that no low temperature reaction is necessary, and the resultant 3-formylphenylboronic acid compound is advantageous in that the degree of purity thereof is high.

EXAMPLE

The present invention will be further explained by the following examples which are not intended to limit the scope of the present invention in any way.

Production Example 1

Preparation and purification of methyl 5-bromo-3-(hydroxymethyl)benzoate (the formula (I))

A three-necked flask having a capacity of 2 liters was charged with 109.2 g of dimethyl 5-bromo-isophthalate and then with 400 ml of tetrahydrofuran (THF), to prepare a solution of dimethyl 5-bromoisophthalate. The solution was mixed with 16.6 g of sodium borohydride and the resultant mixture liquid was agitated while cooling the mixture liquid with ice pieces. Separately, 40.5 ml of methyl alcohol were dissolved in 150 ml of THF, the resultant solution was mixed in the ice-cooled mixture liquid. Then, the resultant reaction mixture liquid was agitated for 5 hours while cooling with ice pieces. The reaction mixture liquid was added with 380 ml of water to terminate the reaction, and then mixed with a 1 mole hydrochloric acid solution to adjust the pH value of the reaction mixture liquid to 7.0. The resultant reaction mixture liquid was subjected to an extraction treatment with 380 ml of ethyl acetate and then with 200 ml of ethyl acetate. The resultant organic extract liquids were mixed with each other, and the resultant mixed extract liquid was washed with 300 ml of water and then with 80 ml of a saturated aqueous common salt solution, and the resultant washed extract liquid was dried with a drying agent consisting of anhydrous magnesium sulfate.

The dried extract liquid was filtered to separate the drying agent, and the resultant filtrate was concentrated. A crude product of the target compound, namely methyl 5-bromo-3-(hydroxymethyl)benzoate was obtained in an amount of 96.5 g. In the crude product, the mass ratio of the target compound, namely methyl 5-bromo-3-(hydroxymethyl) benzoate to the by-product consisting of 5-bromo-3-(hydroxymethyl)benzyl alcohol was 88:10, as determined by NMR measurement.

The crude product was dissolved in 160 ml of methyl alcohol; the resultant solution was placed in a separatory funnel and mixed with 160 ml of water and 1000 ml of xylene; and the resultant mixture liquid was subjected to a phase separation. The resultant organic phase fraction was collected, washed with 160 ml of a solution of methyl alcohol in water in volume ratio of 1:1, then with 160 ml of water and finally with 160 ml of a saturated aqueous common salt solution. The washed organic phase fraction was dried with a drying agent consisting of anhydrous magnesium sulfate. The dried solution was subjected to a filtration procedure to remove the drying agent from the organic phase fraction. Then, the filtrate was concentrated. The target compound, namely, purified methyl 5-bromo-3-(hydroxymethyl)benzoate was obtained in an amount of 81.98 g. The yield thereof was 83.3%. In the resultant purified product, a mass ratio of the target compound, methyl 5-bromo-3-(hydroxymethyl)benzoate to a by-product, namely, 5-bromo-3-(hydroxymethyl)benzyl alcohol was 96:1.8, determined by the NMR measurement. The results of the $^1$H-NMR measurement (200 MHz, δ ppm, CDCl$_3$) were as follows 3.93(s, 3H), 4.74 (d, J=5.6 Hz, 2H)

7.73 (s, 1H), 7.95 (s, 1H), 8.09 (s, 1H).

Production Example 2

Preparation of 3-formylphenylboronic Acid (the Formula (VI)

A three-necked flask with a capacity of 2 liters was charged with 24.9 g of metallic magnesium. Separately, a solution was prepared by dissolving 215.34 g of 3-(dimethoxymethyl)bromobenzene in 1095 ml of THF.

The three-necked flask containing the magnesium metal was further charged with the THF solution in an amount of 75 ml and then with 1.07 ml of a reaction initiator consisting of 1,2-dibromoethane. When an exothermic reaction is initiated in the reaction mixture in the three-necked flask, the remaining amount of the THF solution was gradually dropped into the flask to such an extent that the reaction mixture is moderately refluxed. After the dropping procedure of the THF solution was completed, the resultant reaction mixture liquid in the flask was agitated at room temperature for one hour. A Grignard reagent consisting of a magnesium compound of 3-(dimethoxymethyl) bromobenzene was obtained.

Separately, a three-necked flask having a capacity of 3 liters was charged with 154.8 ml of trimethyl borate and then with 915 ml of THF to prepare a solution of trimethyl borate in THF. The solution was agitated while a nitrogen gas flowed through the flask and the solution was cooled with ice. The ice-cooled THF solution was mixed with the Grignard reagent fed into the 3 liter flask through a stainless steel pipe.

The resultant reaction mixture liquid was agitated for one hour while cooling with ice, and then further mixed with an aqueous sulfuric acid solution prepared from 30 ml of concentrated sulfuric acid and 480 ml of water. The temperature of the resultant admixture liquid was raised to room temperature and, then, the admixture liquid was agitated at this temperature for 2 hours. Thereafter, the agitation was stopped and the resultant reaction mixture liquid was left to stand in the ambient atmosphere for one night.

The precipitate generated in the reaction mixture liquid was removed by filtration and the resultant filtrate was concentrated. The resultant concentration residue was mixed with water in a volume equal to that of the concentration residue, the resultant mixture liquid was agitated at room temperature for one hour. The resultant solid fraction was collected from the mixture liquid by filtration and dried. The target compound 3-formylphenylboronic acid was obtained in an amount of 123.46 g. The yield thereof was 88%. The results of the ¹H-NMR measurement of the resultant target compound (200 MHz, δ ppm, CDCl₃) were as follows.

7.54 (t, J=7.5 Hz, 1H), 7.93 (d, J=6.1 Hz, 1H), 7.9–8.1 (br. d, 1H), 8.2–8.3 (br. s, 1H), 10.04 (s, 1H)

Production Example 3

Preparation of 3-cyanophenylboronic Acid (of the Formula (III))

In a three-necked flask with a capacity 3 liters, 123.4 g of the 3-formylphenylboronic acid prepared in Production Example 2, 68.6 g of hydroxylamine hydrochloride, 1050 ml of formic acid and 112.1 g of sodium formate are placed and mixed with each other. The resultant mixture liquid was heated for 8 hours while refluxing. The resultant reaction mixture liquid was left to stand in the ambient atmosphere for one night. Thereafter, in the case where a precipitate was generated in the reaction mixture liquid, this mixture liquid was agitated while cooling with ice and, in the case where no precipitate was generated in the reaction mixture liquid, the mixture liquid was mixed with a small amount of precipitation seed particles and agitated. From the resultant reaction mixture liquid, the solid precipitate was collected, by filtration and dried. The target compound, 3-cyanophenylboronic acid was obtained in an amount of 82.0 g. The yield thereof was 68%. The results of the ¹H-NMR measurement of the target compound (200 MHz, δ ppm, CDCl₃) were shown below.

7.47 (t, J=7.7 Hz, 1H), 7.69 (d, J=7.9 Hz, 1H), 7.9–8.0 (br. d, 1H), 8.0–8.1 (br. s, 1H)

Example

Preparation of methyl 5-(3-cyanophenyl)-3-formylbenzoate

Step (A) Preparation of methyl 5-bromo-3-formylbenzoate

In a three-necked flask with a capacity of 3 liters, 253.11 g of methyl 5-bromo-3-(hydroxymethyl)benzoate were placed and mixed with 2000 ml of toluene, and the resultant mixture was agitated to prepare a solution. The resultant solution was mixed with 44 g of manganese dioxide, and the resultant reaction mixture liquid was heated to a temperature of 105° C. and agitated for 7 hours. The resultant reaction mixture liquid was allowed to be cooled to room temperature and filtered to remove a solid fraction therefrom, and the resultant filtrate was concentrated. The target compound, methyl 5-bromo-3-formylbenzoate was obtained in an amount of 236.79 g which corresponded to a yield of 94.3%.

The results of the ¹H-NMR (200 MHz, δ ppm, CDCl₃) of the resultant compound were as follows.

3.98 (s, 3H), 8.1–8.3 (m, 1H), 8.3–8.6 (m, 2H), 10.0 (s, 1H)

Step (B) Preparation of methyl 5-(3-cyanophenyl)-3-formylbenzoate

In a three-necked flask with a capacity of 2 liters, 3-cyanophenylboronic acid in an amount of 67.65 g and sodium hydrogen carbonate in an amount of 116.0 g were placed and then a solution of 111.9 g of methyl 5-bromo-3-formylbenzoate prepared in step (A) in 142 ml of dimethyl formamide (DMF) was placed. The resultant mixture liquid in the flask was mixed with 592 ml of DMF and 149 ml of water. The flask was gas-tightly sealed, the air inside the flask was replaced by an argon gas and then 0.2231 g of palladium acetate was fed into the flask. The resultant reaction mixture liquid in the flask was heated to a temperature of 80° C. and agitated at this temperature for 6.5 hours.

Thereafter, the resultant reaction mixture liquid was subjected to a hot-filtration to remove an insoluble fraction from the reaction mixture liquid, and the resultant filtrate was heated to a temperatures of 80° C. and agitated. The heated and agitated filtrate was gradually added with 585 ml of water, and the resultant filtrate mixture was left to cool to room temperature. The precipitate generated in the filtrate mixture was collected by filtration, and the collected precipitate was washed with 590 ml of water and then dried. A crude product of the target compound, methyl 5-(3-cyanophenyl)-3-formylbenzoate was obtained in an amount of 103.15 g which corresponded to a yield of 84.5%.

The crude product was subjected to a purification procedure as follows.

The dried crude product in an amount of 50 g was placed in a three-necked flask with a capacity of 2 liters and mixed with 150 ml of hydrous THF having a water content of 3%. The resultant mixture was heated to a temperature of 80° C. to provide a solution of the crude product. The solution was subjected to a hot-filtration. The filtrate was again heated to a temperature of 80° C. and mixed with 750 ml of 2-propyl alcohol. The resultant mixture liquid was left to cool to room temperature, to recrystallize the target compound. After cooling, the resultant precipitate generated in the cooled mixture liquid was collected by filtration. A purified product of the target compound, methyl 5-(3-cyanophenyl)-3-formylbenzoate was obtained in an amount of 45.19 g which corresponded to a recrystallization yield of 90%. The result of the ¹H-NMR (200 MHz, δ ppm, CDCl₃) of the purified product was as follows.

4.02 (s, 3H), 7.5–7.8 (m, 2H), 7.8–8.0 (m, 2H), 8.2–8.3 (s, 1H), 8.4–8.6 (m, 2H), 10.2 (s, 1H)

INDUSTRIAL APPLICABILITY OF THE INVENTION

The process of the present invention for producing a 5-(3-cyanophenyl)-3-formylbenzoic acid compound enables a 5-(3-cyanophenyl)-3-formylbenzoic acid compound useful as an intermediate of medicines, particularly, inhibitors against selective activated blood coagulation factor X (FX$_a$), to be produced by easy procedures applicable to industrial practice and containing no column chromatography step, with a high yield and with a low cost, and therefore has a high applicability to industrial practice.

What is claimed is:

1. A process for producing a 5-(3-cyanophenyl)-3-formylbenzoic acid compound comprising the steps of:
    reacting a 5-bromo-(3-hydroxymethyl)benzoic acid compound represented by the formula (I):

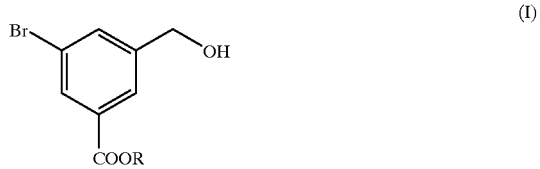

(I)

in which formula (I), R represents a hydrogen atom or a linear or branched chain alkyl group having 1 to 10 carbon atoms, with manganese dioxide, to prepare a 5-bromo-3-formylbenzoic acid compound represented by the formula (II):

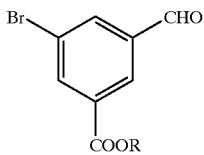

(II)

in which formula (II), R is as defined above; and reacting the resultant 5-bromo-3-formylbenzoic acid compound with 3-cyanophenylboronic acid represented by the formula (III):

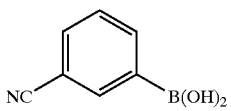

(III)

in the presence of a palladium complex, to prepare a 5-(3-cyanophenyl)-3-formylbenzoic acid compound represented by the formula (IV):

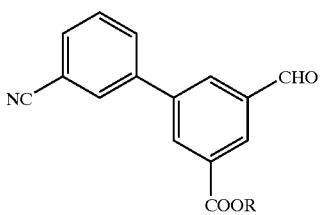

(IV)

in which formula (IV), R is as defined above.

2. The process for producing a 5-(3-cyanophenyl)-3-formylbenzoic acid compound as claimed in claim 1, wherein the 3-cyanophenylboronic acid represented by the formula (III) is one prepared by reacting 3-formylphenylboronic acid represented by the formula (V):

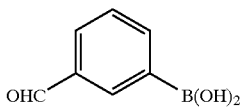

(V)

with hydroxyamine hydrochloride.

3. The process for producing a 5-(3-cyanophenyl)-3-formylbenzoic acid compound as claimed in claim 2, wherein the 3-formylphenylboronic acid represented by the formula (V) is one prepared by reacting a 3-(dialkoxymethyl)bromobenzene represented by the formula (VI):

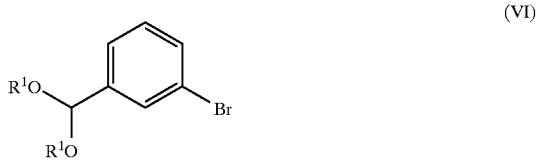

(VI)

in which formula (VI), $R^1$ represents a linear or branched chain alkyl group having 1 to 4 carbon atoms, with magnesium metal to prepare an organic magnesium compound of the 3-(dialkoxymethyl)bromobenzene; and then further reacting the resultant organic magnesium compound with a trialkyl borate.

4. The process for producing a 5-(3-cyanophenyl)-3-formylbenzoic acid compound as claimed in claim 1, wherein the 5-bromo-3-(hydroxymethyl)benzoic acid compound represented by the formula (I) is one prepared by reacting a 5-bromoisophthalic acid compound represented by the formula (VII):

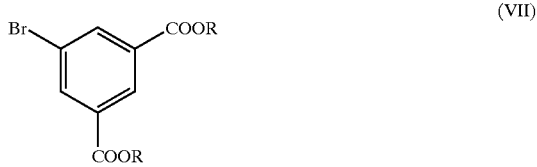

(VII)

in which formula (VII), R is as defined above, with sodium borohydride.

5. The process for producing a 5-(3-cyanophenyl)-3-formylbenzoic acid compound as claimed in claim 4, wherein the 5-bromo-3-(hydroxymethyl)benzoic acid compound prepared by the reaction of the 5-bromoisophthalic acid compound represented by the formula (VII) with sodium borohydride, is purified by using a mixed solvent comprising an alcohol and a benzene derivative.

* * * * *